US00PP10318P

United States Patent [19]

Baetcke

[11] Patent Number: Plant 10,318

[45] Date of Patent: Apr. 7, 1998

[54] AZALEA PLANT NAMED 'AQUARELL'

[76] Inventor: Hanno Baetcke, Gartenbau Verheyen-Baetcke GbR Nordring 172-174, 47661 Issum, Germany

[21] Appl. No.: 780,629

[22] Filed: Jan. 8, 1997

[51] Int. Cl.[6] ..... A01H 5/00

[52] U.S. Cl. ..... Plt./55

[58] Field of Search ..... Plt./55, 56, 57

*Primary Examiner*—James R. Feyrer

*Attorney, Agent, or Firm*—C. A. Whealy

[57] ABSTRACT

A new and distinct cultivar of Azalea plant named 'Aquarell', characterized by its dark green leaves and numerous and large white-colored flowers with dark hot pink-speckled edges.

2 Drawing Sheets

The present invention relates to a new and distinct cultivar of Azalea, botanically known as *Rhododendron simsii*, and hereinafter referred to by the cultivar name Aquarell.

The new cultivar was discovered and selected in 1990 by the inventor as a naturally-occurring petal color mutation of the *Rhododendron simsii* cultivar Helmut Vogel (not patented) at his nursery in Issum, Germany.

Plants of the new Azalea are similar to plants of the parent cultivar Helmut Vogel in all plant characteristics with the exception of petal color. Plants of the cultivar Helmut Vogel have red-colored petals whereas plants of the new Azalea have white-colored petals with dark hot pink-speckled edges.

Asexual reproduction of the new cultivar by terminal cuttings taken at Issum, Germany, has shown that the unique features of this new Azalea plant are stable and reproduced true to type in successive generations of asexual reproduction.

The following traits have been repeatedly observed and are determined to be the unique characteristics of 'Aquarell'. These characteristics in combination distinguish the new Azalea plant as a new and distinct cultivar:

1. Dark green leaves.
2. Numerous and large white-colored flowers with dark hot pink-speckled edges giving a bi-colored appearance.

The new Azalea plant has not been observed under all possible environmental conditions. The phenotype may vary significantly with variations in environment such as temperature, light level, nutrition and water status without, however, any variance in genotype.

The accompanying colored photographs illustrates the overall appearance of the new cultivar, showing the colors as true as it is reasonably possible to obtain in colored reproductions of this type.

The first photograph comprises a side perspective view of typical plant of 'Aquarell', The second photograph comprises a close-up view of a typical flowers of 'Aquarell'.

Flower and foliage colors in the photograph may appear different from the actual colors due to light reflectance.

The following observations, measurements, values, and comparisons describe plants grown in Salinas, Calif., in 12-cm containers under glass with day temperatures ranging from 24° to 27° C., night temperatures ranging from 13° to 16° C., and light levels averaging 4,500 footcandles.

In the following description, color references are made to The Royal Horticultural Society Colour Chart except where general terms of ordinary dictionary significance are used.

Classification:

*Botanical.*—*Rhododendron simsii* cv. 'Aquarell'.

Parentage: Naturally-occurring petal color mutation of *Rhododendron simsii* cv. 'Helmut Vogel' (not patented).

Propagation:

*Type.*—By terminal cuttings.

*Time to develop roots.*—60 days at temperatures of 22° C.

*Rooting habit.*—Moderately vigorous and finely-branched.

Plant description:

*Plant form and growth habit.*—Perennial, evergreen, outwardly spreading, inverted triangle. Moderate vigor.

*Branching habit.*—Freely branching, three to four lateral branches develop after removal of terminal apex.

*Plant height, soil level to top of flowers.*—About 17 cm.

*Plant diameter, area of spread.*—About 29 cm.

*Lateral branch description.*—Length: About 9.5 cm. Diameter: About 4 mm. Color: 166B. Texture: Sparsely pubescent.

Foliage description:

*Arrangement.*—Alternate, single.

*Leaf size, largest leaves.*—Length: 4 to 5 cm. Width: 2.5 to 3 cm.

*Leaf shape.*—Elliptic.

*Leaf apex.*—Cuspidate.

*Leaf base.*—Attenuate.

*Margin type.*—Entire.

*Texture.*—Leathery, pubescent on both surfaces.

*Color.*—Young foliage, upper surface: Darker than 147A. Young foliage, lower surface: 147B. Mature foliage, upper surface: Darker than 147A. Mature foliage, lower surface: 147B. Venation, upper surface: 147B. Venation, lower surface: 147B.

*Petiole.*—Length: About 6 mm. Diameter: About 2 mm. Color: 147C.

Flower description:

*Natural flowering season.*—Spring after sufficient cool period.

*Flower arrangement.*—Flowers arranged singly at terminals with usually five to seven flowers per terminal. Flowers face upward and outward. Freely flowering.

*Flower appearance.*—Star-shaped semi-double. White colored-petals with dark hot pink-speckled edges giving a bi-color appearance. Flowers persistent.

*Flower diameter.*—About 9.5 cm.

*Flower longevity.*—Seven to nine days depending on temperature.

*Flower bud.*—Rate of opening: About three days depending on temperatures. Length: About 1.7 cm. Diameter: About 1 cm. Shape: Ovoid. Color: 144B/144C.

*Petals.*—Appearance: Satiny. Texture: Smooth. Arrangement: Semi-double. Outer corolla consists of five fused petals and inner corolla consists of five to seven fused stamenoidal petaloids. Shape: Elliptic with rounded apex. Margin: Entire, undulating. Size: Length: About 6 cm. Width: About 3.7 cm. Color: When opening, upper and lower surfaces: White with dark hot pink, 57A, speckles at margin and extending about 7 mm inward from the margin. Random and sparse dark hot pink, 57A, speckles in center of petals. 145A/145B at base of petals. Fully opened, upper and lower surfaces: White with dark hot pink, 57A, speckles at margin and extending about 7 mm inward from the margin. Random and sparse dark hot pink, 57A, speckles in center of petals. Petal color does not fade. Throat (inside surface): Speckles of 145A.

*Sepals.*—Appearance: Five sepals fused into a star-shaped calyx. Texture: Pubescent. Shape: Linear. Apex: Attenuate. Margin: Entire. Color, upper and lower surfaces: 144A.

*Peduncles.*—Length: About 1 cm. Angle: Upright. Strength: Flexible. Color: 144B.

*Reproductive organs.*—Androecium: Stamen number: Five, usually fused into petaloids. Anther shape: Oblong. Anther size: About 2 mm. Anther color: Golden orange. Amount of pollen: Moderate. Pollen color: Golden. Gynoecium: Pistil number: One. Pistil length: About 3.7 cm. Stigma shape: Rounded. Stigma color: 145A. Style length: About 3 cm. Style color: Light green to white. Ovary color: Green, 143A.

Disease resistance: No known Azalea diseases observed to date on plants grown under commercial greenhouse conditions.

Seed production: Seed production has not been observed.

It is claimed:

1. A new and distinct Azalea plant named 'Aquarell', as illustrated and described.

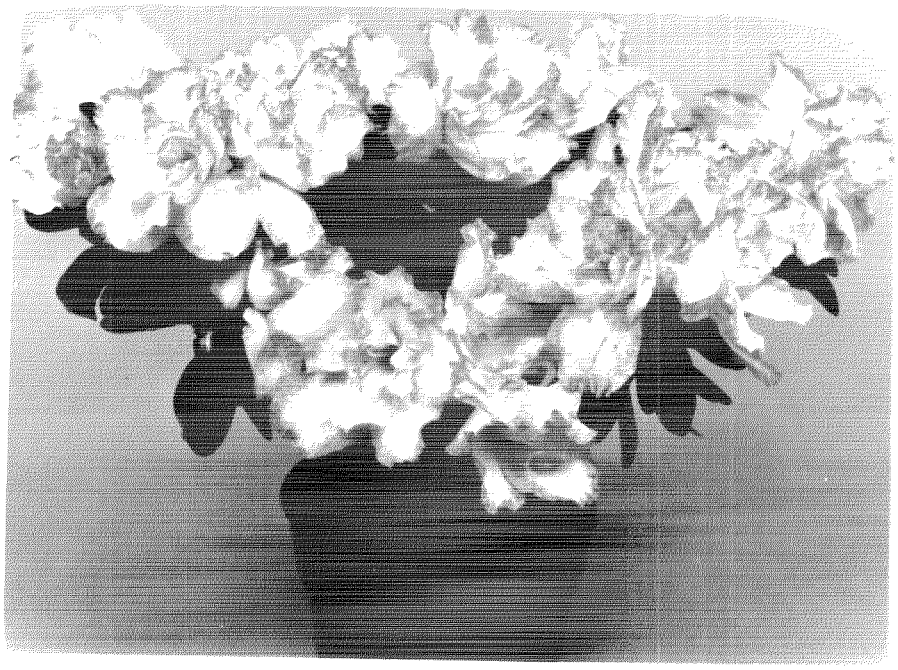

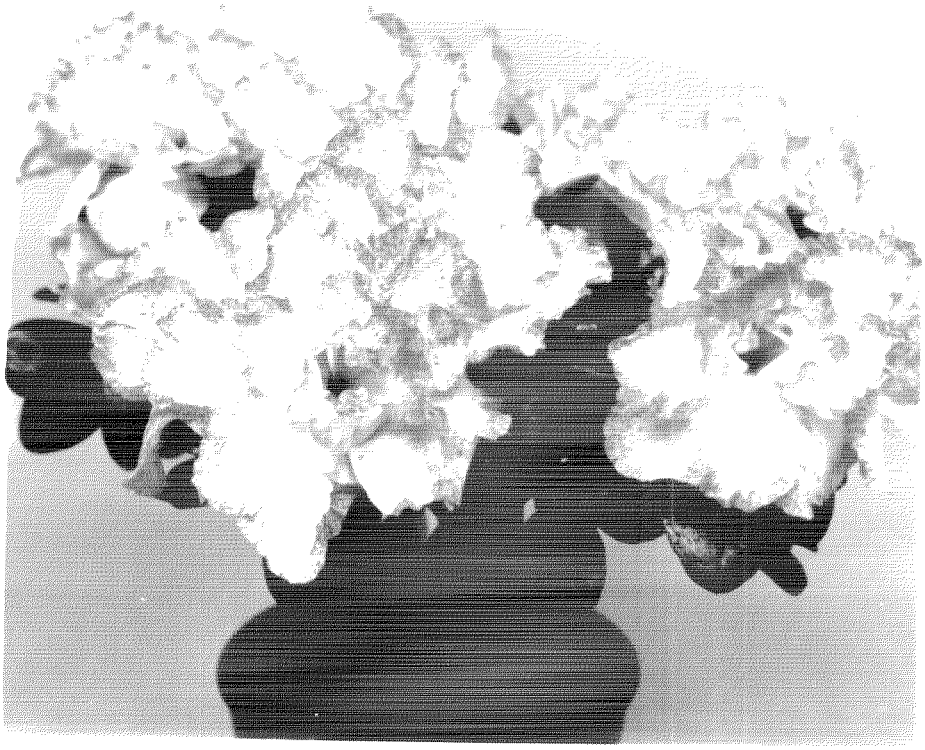

* * * * *